United States Patent [19]

Marquis et al.

[11] Patent Number: 4,703,027

[45] Date of Patent: Oct. 27, 1987

[54] MOLYBDENUM/ALKALI METAL/ETHYLENE GLYCOL COMPLEXES USEFUL AS EPOXIDATION CATALYSTS

[75] Inventors: Edward T. Marquis, Austin; John R. Sanderson, Leander; Kenneth P. Keating, Georgetown, all of Tex.

[73] Assignee: Texaco Inc., White Plains, N.Y.

[21] Appl. No.: 916,076

[22] Filed: Oct. 6, 1986

[51] Int. Cl.$^4$ .............................................. B01J 31/22
[52] U.S. Cl. ..................................... 502/171; 556/57; 549/529; 568/909.8
[58] Field of Search ........................... 502/171; 556/57

[56] References Cited

U.S. PATENT DOCUMENTS

| | | | |
|---|---|---|---|
| 2,795,552 | 6/1957 | Abbott et al. | 556/57 X |
| 3,285,942 | 11/1966 | Price et al. | 556/57 |
| 3,668,227 | 6/1972 | Mattucci et al. | 556/57 |
| 3,956,180 | 5/1976 | Cavitt | 502/171 |
| 3,991,090 | 11/1976 | Hagstrom et al. | 556/57 |
| 4,009,122 | 2/1977 | Lines et al. | 556/57 X |

*Primary Examiner*—Patrick P. Garvin
*Attorney, Agent, or Firm*—Jack H. Park; Kenneth R. Priem

[57] ABSTRACT

Complexes are made by reacting a solid ammonium molybdate and a solid alkali metal molybdate with ethylene glycol. Stripping of water of reaction subsequent to complex formation is preferred. The ratio of moles of alkylene glycol to total gram atoms of molybdenum should be in the range from about 7:1 to about 20:1 and the ratio of gram atoms of molybdenum in the ammonium molybdate to gram atoms of molybenum in the alkali metal molybdenum should be in the range of about 1:1 to about 20:1. Solutions of the complexes are excellent catalysts for the reaction of propylene with an organic hydroperoxide such as tertiary butyl hydroperoxide to form proplyene oxide and tertiary butyl alcohol.

16 Claims, No Drawings

4,703,027

MOLYBDENUM/ALKALI METAL/ETHYLENE GLYCOL COMPLEXES USEFUL AS EPOXIDATION CATALYSTS

BACKGROUND OF THE INVENTION

1. Field of the Invention

The invention relates to the preparation of molybdenum/alkali metal/ethylene glycol complexes and to the manufacture of propylene oxide and tertiary butyl alcohol by the molybdenum/sodium/ethylene glycol catalyzed reaction of propylene with tertiary butyl hydroperoxide useful as olefin epoxidation catalysts.

2. Prior Art

The epoxidation of olefins to give various epoxide compounds has long been an area of study by those skilled in the art. It is well known that the reactivities of the various olefins differ with the number of substituents on the carbon atoms involved in the double bond. Ethylene itself has the lowest relative rate of epoxidation, with propylene and other alpha olefins being the next slowest. Compounds of the formula $R_2C=CR_2$, where R simply represents alkyl or other substituents, may be epoxidized fastest. Thus, the more substituents on the double bond carbons, the easier it is to epoxidize across that bond.

The production of ethylene oxide from ethylene has long been accomplished by reaction with molecular oxygen over a silver catalyst. Numerous patents have issued on various silver-catalyzed processes for the production of ethylene oxide. Unfortunately, the silver catalyst route will not work for olefins other than ethylene. For a long time the commercial production of propylene oxide could only be accomplished via the cumbersome chlorohydrin process.

Another commercial process for the manufacture of substituted epoxides from alpha olefins such as propylene was not discovered until John Kollar's work in the 1960s. His U.S. Pat. No. 3,351,635 taught that an organic epoxide compound could be made by reacting an olefinically unsaturated compound with an organic hydroperoxide in the presence of a molybdenum, tungsten, titanium, columbium, tantalum, rhenium, selenium, chromium, zirconium, tellurium or uranium catalyst. Kollar's U.S. Pat. No. 3,350,422 teaches a similar process using a soluble vanadium catalyst.

The Kollar process is a coproduct process wherein the olefin and the hydroperoxide are catalytically reacted to provide an epoxide corresponding to the olefin and an alcohol corresponding to the hydroperoxide. A wide variety of epoxides and alcohols can be prepared in this manner. The process is practiced commercially in the manufacture of propylene oxide from propylene.

Kollar's work has been recognized as extremely important in the development of a commercial propylene oxide process that did not depend on the chlorohydrin route. It has been recognized that Kollar's catalytic route (in which a soluble molybdenum compound is the preferred catalyst) has a number of problems. For example, when propylene is the olfin to be epoxidized, various propylene dimers, sometimes called hexenes are formed as byproducts. Besides being undesirable in that the best use of propylene was not made, problems are encountered in separating the desired propylene oxide from the product mix. In addition, the molybdenum catalyst may not be stable or the recovery of the catalyst for recycle may be poor.

Various avenues of investigation have been explored in attempts to improve on the molybdenum-catalyzed epoxidation of propylene. One technique was to try to improve on the catalyst itself. Patents which cover the preparation of various molybdenum epoxidation catalysts include U.S. Pat. No. 3,362,972 to Kollar. There a hydrocarbon soluble salt of molybdenum or vanadium may be made by heating a molybdenum compound in which molybdenum has a valence of $+6$, or a vanadium compound in which vanadium has a valence of $+5$, with a carobxylic acid of from 4 to 50 carbon atoms having at least 4 carbon atoms per carboxylic group. U.S. Pat. No. 3,578,690 to Becker discloses that molybdenum acid salts may be made by directly reacting a carboxylic acid with a molybdenum compound while removing the water that is formed.

The reaction of molybdenum trioxide with monohydric saturated alcohols having 4 to 22 carbon atoms or with a mono- or polyalkylene glycol monoalkyl ether or mixtures thereof to make olefin epoxidation catalysts is described in U.S. Pat. No. 3,480,563 to Bonetti et al. These catalysts have only 0.07 to 0.93% molybdenum, which is a molybdenum content too low for commercial use. Bonetti et al. do not realize the importance of the ratio of alcohol to molybdenum compound reactants with respect to maximizing molybdenum content yet providing a soluble, active epoxidation catalyst. They also do not indicate any benefit from adding ammonium hydroxide to the preparation, an important factor discovered when molybdenum trioxide is reacted with 2-ethyl-1-hexanol.

In U.S. Pat. No. 4,434,975 to ARCO, investigators found that molybdenum catalysts could be made from saturated alcohols or glycols having one to four carbon atoms, such as ethylene glycol and propylene glycol, by reacting them with molybdenum metal and an organic hydroperoxide, peroxide, or $H_2O_2$. Molybdenum compounds prepared by reacting an ammoniumcontaining molybdate with a hydroxy compound, for example, an organic primary or secondary alcohol, a glycol or a phenol, are described in U.S. Pat. No. 3,784,482 and 3,787,329 to Cavitt.

Further, U.S. Pat. No. 3,573,226 to Sorgenti discloses that molybdenum-containing epoxidation catalyst solutions may be made by heating molybdenum powder with a stream containing unreacted tertiary butyl hydroperoxide and polyhydric compounds of from about 200 to 300 molecular weight and having from 4 to 6 hydroxyl groups per molecule. These catalysts are used for the epoxidation of propylene according to U.S. Pat. No. 3,666,777 to Sorgenti.

U.S. Pat. No. 3,953,362 to Lines et al. reveals that novel molybdenum epoxidation catalysts may be prepared by reacting an oxygen-containing molybdenum compound with hydrogen peroxide and an amine and optionally water or an alkylene glycol at elevated temperatures. Similar catalysts are prepared by reacting an oxygen-containing molybdenum compound with an amine and an alkylene glycol at elevated temperatures according to U.S. Pat. No. 4,009,122 also to Lines et al.

U.S. Pat. No. 3,668,227 to Mattucci et al. also concerns molybdenum glycol catalysts prepared from molybdenum acetyl acetonate and isolated as solids. When the materials are used as epoxidation catalysts, they must be employed in solution with a hydrocarbon solvent. Molybdenum derivative compounds also useful as epoxidation catalysts may be prepared by reacting an oxygen-containing molybdenum compound such as molybdenum acetylacetonate, molybdic acids and molybdenum oxides with an organic compound having vicinal hydroxyl groups in the presence of a hydrohalic acid such as hydrofluoric acid, hydrochloric acid and the like, according to U.S. Pat. No. 3,991,090 to Hagstrom et al.

Kollar U.S. Pat. Nos. 3,860,662 and 3,947,500 disclose a modification of the epoxidation process wherein the epoxidation reactor effluent, which is acidic, is treated with a base such as sodium bisulfite or sodium hydroxide in order to decrease reaction product dehydration during the distillation of the reactor effluent.

In our laboratories the preparation and utilization of epoxidation catalysts has been studied. Copending Marquis et al. U.S. patent application Ser. No. 687,701, now U.S. Pat. No. 4,626,596, entitled "Synthesis of Molybdenum/Alkylene Glycol Complexes Useful as Epoxidation Catalyst" is directed to the provision of soluble molybdenum/alkylene glycol complexes by the reaction of an ammonium-containing molybdenum compound such as ammonium heptamolybdate tetrahydrate with a glycol such as ethylene glycol or propylene glycol. Copending Marquis et al. U.S. patent application Ser. No. 804,132, now U.S. Pat. No. 4,654,427 entitled "Synthesis of Molybdenum Oxide/Alkanol Complexes" discloses the preparation and utilization of soluble molybdenum catalysts made by reacting a molybdenum oxide with an alkanol in the presence of ammonium hydroxide. Copending Marquis et al. U.S. patent application Ser. No. 804,131, now U.S. Pat. No. 4,650,886 entitled "Synthesis of Ammonium Molybdate/Alkanol Complexes" is directed to the preparation and utilization of soluble molybdenum catalysts prepared by reacting an alkanol with an ammonium molybdate.

Although the results obtained have been generally satisfactory, there is still need for improvement.

SUMMARY OF THE INVENTION

The invention concerns molybdenum/alkali metal/ethylene glycol complexes made by reacting an ammonium-containing molybdenum compound and an alkali metal molybdate with an ethylene glycol. The complexes are useful as epoxidation catalysts and the molybdenum/sodium ethylene glycol catalysts have been found to be particularly useful as propylene epoxidation catalysts.

DETAILED DESCRIPTION OF THE PREFERRED EMBODIMENTS

The improvements in the complexes of this invention relate to the discovery that the incorporation of an alkali metal into a molybdenum/ethylene glycol complex provides a storage stable solids-free solution of the complex in unreacted ethylene glycol that has significantly reduced acidity.

Molybdenum/ethylene glycol epoxidation catalysts, including molybdenum/ethylene glycol catalysts disclosed in copending Marquis et al. U.S. patent application Ser. No. 687,701, now U.S Pat. No. 4,626,596 are inherently acidic. We find that there is a general tendency for molybdenum/ethylene glycol catalysts to increase in activity as the acidity is increased, such that the conversion of the hydroperoxide feed component is increased but that the increase in conversion is normally accompanied by a decrease in selectivity.

In accordance with the present invention, it has been discovered that if a controlled amount of an alkali metal molybdate (preferably sodium molybdate) is incorporated into the complex so as to provide a molybdenum/alkali metal/ethylene glycol complex, the resultant complex will be less acidic than the corresponding molybdenum/ethylene glycol complex.

It has also been discovered in accordance with the present invention that the use of excessive quantities of solvent (e.g., ethylene glycol) is deleterious. It is necessary to provide a solvent for the molybdenum/sodium/ethylene glycol complex, but the amount of solvent (e.g., excess ethylene glycol) that is utilized can be kept to a minimum with the practice of the present invention.

The high molybdenum content and the alkali metal content should be achieved by adjusting the ratio of glycol to gram atoms of molybdenum. If an excess of glycol is used and is then removed by distillation to concentrate the molybdenum content of the complex, the complex will perform poorly as an epoxidation catalyst in that the selectivity based on the organic hydroperoxide consumed will be poor and the tendency of solids to precipitate from the catalyst solution will be increased.

The molybdenum compounds to be used as starting materials for the present invention are of two types; namely, those molybdenum compounds that contain ammonium ligands as well as oxygen, and alkali metal molybdates and hydrates thereof.

The ammonium-containing compounds include compounds such as ammonium heptamolybdate, ammonium dimolybdates, etc. and hydrate forms thereof such as ammonium heptamolybdate tetrahydrate (the preferred method for having water present). Other ammonium heterpoly molybdates and mixtures thereof are also useful.

The second type of molybdenum compound is an alkali metal molybdate such as sodium molybdate, potassium molybdate, cesium molybdate or a hydrate thereof, which is suitably used in the commercially available powdered solid form.

Ethylene glycol constitutes the third co-reactant used in making the molybdenum complexes of this invention.

Further, it has been found that the ratio of glycol (moles of glycol) to total gram atoms of molybdenum and the ratio of molybdenum from the different sources are both important. In addition, the temperature used in preparing the complex is also important in determining the amount of molybdenum in the complex, the ease of processing and the storage stability of the complex with respect to the precipitation of solids. Also important is the choice of the nonalkali metal-containing compound. For example, when molybdenum trioxide is used in place of ammonium heptamolybdate (AHM) or ammonium dimolybdate (ADM) in reaction with ethylene glycol (EG), poorer results were obtained. The complex also gave poor results as an epoxidation catalyst with respect to propylene oxide selectivity.

For the ethylene glycol component of the complex, the preferred reactant ratios are 7:1 to 20:1 expressed in terms of moles of glycol to total gram atoms of molybdenum from both molybdenum sources. An especially preferred range of moles of ethylene glycol to total gram atoms of molybdenum is 8:1 to 16:1.

For the alkali metal molybdate component of the complex, the preferred reactant ratios are such that the gram atoms of molybdenum derived from the alkali metal molybdate never exceed the gram atoms of molybdenum derived from the ammoniumcontaining component (i.e., the ratio of gram atoms of molybdenum derived from the ammonium-containing component to the gram atoms of molybdenum derived from the alkali metal molybdate should be 1/1 or greater than 1/1).

To provide the best complex in terms of molybdenum and alkali metal content, ease of processing and stability upon standing, the proportion of water remaining in the complex should be in the range of 0.1 to 2 wt. %. The reaction temperature to make the complexes of the present invention should be between about 50° and 150° C., preferably 90° to 120° C., and the pressure should be atmospheric. High reaction temperatures, on the order of 165° to 180° C. lead to sharply reduced molybdenum contents and large formation of solids. With the technique of this invention, liquid complexes with molybdenum contents of 6 to 24% are possible. Typically, these molybdenum contents are 10 to 20%, normally about 12 to 16%, which remains greater than that obtainable by prior methods.

The reaction time for catalyst preparation will vary, depending on the chemical identity and concentration of the reactants. In general, reaction times in the range of about 0.2 to about 2 hours may be used. Normally a reaction time of 0.5 to 1.5 hours, e.g., about one hour, is sufficient.

Generally, minimal filtration is required for the best complexes of this invention because few, if any, solids will be formed during the preparation of the complexes of the present invention. When clear solutions of the complex are formed, a filtration step is not necessary. In a preferred embodiment, the reactants are heated to about 90° to 120° C. for about one hour, cooled and then subjected to a vacuum of 10 to 100 mm Hg for 30 to 60 minutes to remove water and ethylene glycol. The temperature of the pot should be raised to about 90° to 110° C. during the stripping and the pressure should be adjusted to achieve and maintain this temperature. Sufficient overhead is removed so that the complex bottoms amount to about 80 to 95 wt. % of the charge and the water content of the catalyst is preferably in the 0.1 to 2 wt. % range. Generally, the water content of the final complex should be between about 0.1 and 6.0 wt. %, particularly for epoxidation purposes.

If excess water is left in these complexes and they are not stripped, the selectivities which they give when used as epoxidation catalysts remain excellent, but two serious problems result. One, solids form when the catalyst is mixed with the hydroperoxide/alcohol reactant solution, and two, the complex is relatively unstable and may precipitate solids at any time. Therefore, vacuum stripping after the digestion step is highly preferred.

It should be noted that these complexes are surprisingly simple to make and require no corrosive acids, amines, etc. They are made at very mild temperatures and with short reaction times. The complexes require very little or no filtration and can be stored for significant periods of time without precipitation of solids. In addition, the processing costs and reactant costs to make these complexes are low.

It is well known that soluble molybdenum complexes efficiently catalyze the epoxidation of propylene to propylene oxide in the presence of t-butyl hydroperoxide. However, the ethylene glycol alkali metal/molybdenum complexes of this invention surprisingly give selectivities to propylene oxide in such reaction on the order of 98 to 99% and higher at TBHP conversions of about 98 to 98.4% while providing minimal propylene dimer production and very low methyl formate production.

The epoxidations are typically conducted by reacting an olefin with an organic hydroperoxide in the presence of a catalyst and a solvent. Preferably, the olefin is propylene and the hydroperoxide is TBHP. With these reactants, the desired product is propylene oxide (PO). As noted above, the catalyst is usually incorporated into one or the other of the reactants prior to introduction to the reactor.

Preferably, the catalyst concentration is from 100 to 600 ppm based on the combination of the propylene and the tertiary butyl hydroperoxide. Further, the reaction should be conducted at a temperature in the range of 50° to 180° C., preferably 90° to 140° C. and especially in the range of about 100° to 130° C. An unusual aspect is that the preferred mole ratio of olefin to hydroperoxide is unusually low, on the order of from about 0.9:1 to 3.0:1. All of these characteristics, together with using the complexes of this invention as catalysts, provide an epoxidation process that gives excellent results.

Specifically, it was found that these very high molybdenum concentration ethylene glycol/alkali metal complexes are far better in propylene epoxidations, using TBHP, than corresponding complexes with low molybdenum concentrations, provided that the complexes of this invention are made in the manner described above.

Another preferred embodiment of the epoxidations involves conducting the reaction in two stages, approximately equal in length, with the first stage at a lower temperature than the second stage. For instance, the first hour of reaction should preferably be conducted at a temperature in the range of 50° to 120° C. followed by the second and last hour of reaction at about 120° to 150° C.

CATALYST PREPARATIONS

The following examples will illustrate typical preparations of the molybdenum/alkali metal/ethylene glycol complexes of the present invention.

Example 1 (Run 5990-66, Table I)

To a 500-ml round bottomed flask equipped with a mechanical stirrer, thermometer, $N_2$ purge, K-head and condenser was added 248 g EG (4.0 moles), 53.8 g ammonium dimolybdate (ADM, 0.3288 g atoms moly) and 3.43 g sodium molybdate (0.0166 g atoms moly). The mole ratio of EG/g atoms moly from ADM/g atoms moly from $Na_2MoO_4$ was 11.6/0.95/0.05. The reaction mixture was heated to 100° C. and held at 100° C. for 1.0 hour. The reaction mixture was clear, light yellow. It was cooled to 45° C. A vacuum was pulled on the system through the receiver flask, cooled in ice water. The reaction mixture was heated to 100° C. again. The vacuum was 30 mm when 100° C. was reached. The reaction mixture was held at 100° C. for 10 min. while water was removed, the vacuum improving from 30 mm to 15 mm. The heat was turned off after 10 minutes at 100° C. under vacuum. The overhead weighed 15.0 g (11.88% water). The cold trap weighed 5.8 g (83.06% $H_2O$). The product catalyst was clear and contained no solids and weighed 275.4 g. The molybdenum content of the catalyst was 12.1 wt. % and the sodium content was 0.164%. The product catalyst contained 2.04% $H_2O$, 0.87% $N_2$ and had an acid number of 131.96 mg KOH/g sample.

Note: EG=ethylene glycol; ADM=ammonium dimolybdate. ADM analyzed twice and average=58.65% molybdenum. $Na_2MoO_4$ analyzed twice and average was 46.75% molybdenum.

Example 2 (Run 5990-67, Table I)

In an experiment similar to the above Example 1, 248 g EG (4.0 moles) was reacted with 53.8 g ADM (0.3288 g atoms molybdenum) and 4.03 g of sodium molybdate hydrate (0.0166 g atoms of molybdenum). The mole ratio of EG to g atoms of molybdenum from ADM to g atoms of molybdenum from sodium molybdate was 11.6/0.95/.05. The overhead weighed 20.7 g (and was 6.40% $H_2O$). The cold trap weighed 8.3 g and was 94.25% $H_2O$. The catalyst product weighed 268.5 g and contained 11.9% molybdenum. The sodium content of the catalyst was 1600 ppm (0.160%) and the product catalyst contained 0.92% $H_2O$ and the % N by Kjeldahl was 0.99%. The acid number was 134.13 mg KOH/g catalyst sample. $Na_2MoO_4$ $2H_2O$ was analyzed twice and the average=41.55%.

Example 3

Additional catalysts were prepared using the same apparatus and procedure as in Examples 1 and 2, except that in some examples the holding period was increased at 100° C. under vacuum to insure $H_2O$ removed. In examples 5990-68 and 6990-69 (Table I) the product catalyst solution was solids free. In examples 5990-71, 5990-73 and 6032-7 (Table I), although 0.2 and 0.3 g atom molybdenum came from $Na_2MoO_4.2H_2O$, the catalyst remained solids free. Under the same conditions, $Na_2MoO_4$ (anhydrous) afforded catalyst with solids (runs 5990-70, -72 and 6032-6, Table I). At mole ratios of 11.5-11.7/0.6/0.4 EG/g atoms molybdenum from ADM/g atoms molybdenum from $Na_2MoO_4$ or $Na_2MoO_4.2H_2O$, there were always solids at the end of the preparation. Increasing the amount of $Na_2Mo_4$ or $Na_2MoO_4.2H_2O$ led to gradually decreasing molybdenum content in the catalyst.

Note: As the amount of $Na_2MoO_4$ and/or $Na_2MoO_4$ $2H_2O$ increased, the acid number of the catalyst decreased. Lab notebook series 5990-66 to 5990-81.

Example 5990-65 (Control Run, Table I)

Made similar to the above example except no $Na_2MoO_4$ or $Na_2MoO_4.2H_2O$ was used, only ADM.

The foregoing examples and the results obtained are summarized in Table I.

TABLE I[1]

Moly Catalysts from EG and Mixed Moly Sources Such as ADM and $Na_2MoO_4$ or ADM and $Na_2MoO_4.2H_2O$ - Incorporation of Sodium

| NB Run # | ADM[2] Grams (GAMoly)[4] | $Na_2MoO_4$[3] Grams (GAMoly)[4] | $Na_2MoO_4.2H_2O$ Grams (GAMoly)[4] | Moles EG/GAMoly ADM/GAMoly from $Na_2MoO_4$[4] | Stripping Conditions Temp C. | Time |
|---|---|---|---|---|---|---|
| 5990-65 Control | 56.67 (0.3466) | 0 0 | 0 0 | 11.54/1/0 | 50-100 100 | 15 10 |
| 5990-66 | 53.83 (0.3288) | 3.433 (0.0166) | 0 0 | 11.6/.95/.05 | 45-100 100 | 10 10 |
| 5990-67 | 53.83 (0.3288) | 0 0 | 4.033 (0.0175) | 11.6/.95/.05 | 35-100 100 | 20 10 |
| 5990-68 | 51.00 (0.3118) | 6.867 (0.0335) | 0 0 | 11.6/.90/.10 | 80-100 100 | 8 7 |
| 5990-69 | 51.00 (0.3118) | 0 0 | 8.067 (0.0349) | 11.5/.90/.10 | 65-100 100 | 25 10 |
| 5990-70 | 45.33 (0.2771) | 13.73 (0.0669) | 0 0 | 11.6/.81/.19 | 45-100 100 | 15 15 |
| 5990-71 | 45.33 (0.2771) | 0 0 | 16.13 (0.0698) | 11.5/.80/.20 | 70-100 100 | 10 10 |
| 5990-72 | 39.67 (0.2425) | 20.60 (0.1004) | 0 0 | 11.7/.71/.29 | 75-100 100 | 13 13 |
| 6032-6 | 39.60 (0.2421) | 20.60 (0.1004) | 0 0 | 11.7/.71/.29 | 40-100 100 | 15 67 |
| 5990-73 | 39.67 (0.2425) | 0 0 | 24.20 (0.1048) | 11.5/.70/.30 | 40-100 100 | 15 13 |
| 6032-7 | 39.60 (0.2421) | 0 0 | 24.20 (0.1048) | 11.5/.70/.30 | 77-100 100 | 10 10 |
| 5990-74 | 34.00 (0.2073) | 27.47 (0.1338) | 0 0 | 11.7/.61/.39 | 80-100 100 | 10 35 |
| 6032-8 | 34.00 (0.2078) | 27.47 (0.1338) | 0 0 | 11.7/.61/.39 | 50-100 100 | 15 80 |
| 5990-75 | 34.00 (0.2078) | 0 0 | 32.27 (0.1398) | 11.5/.60/.40 | 80-100 100 | 10 25 |
| 6032-9 | 34.00 (0.2078) | 0 0 | 32.27 (0.1398) | 11.5/.60/.40 | 70-100 100 | 10 55 |
| 6032-10 | 28.30 (0.1730) | 34.30 (0.1671) | 0 0 | 11.8/.51/.49 | 30-100 100 | 15 75 |
| 6032-11 | 28.30 (0.1730) | 0 0 | 40.30 (0.1745) | 11.5/.50/.50 | 70-100 100 | 18 100 |
| 6032-12 | 22.70 (0.1388) | 41.20 (0.2008) | 0 0 | 11.8/.41/.59 | 83-100 100 | 10 75 |
| 6032-13 | 22.70 (0.1388) | 0 0 | 48.40 (0.2096) | 11.5/.40/.60 | 78-100 100 | 10 40 |
| 5990-76 | 17.00 (0.1039) | 48.07 (0.2342) | 0 0 | 11.8/.31/.69 | 50-100 100 | 15 40 |
| 6032-14 | 17.00 (0.1039) | 48.00 (0.2339) | 0 0 | 11.8/.31/.69 | 40-100 100 | 15 70 |
| 5990-77 | 17.00 (0.1039) | 0 0 | 56.47 (0.2446) | 11.5/.30/.70 | 75-100 100 | 10 45 |
| 6032-15 | 17.00 (0.1039) | 0 0 | 56.50 (0.2447) | 11.5/.30/.70 | 80-100 100 | 15 90 |
| 6032-16 | 11.33 (0.0693) | 54.93 (0.2677) | 0 0 | 11.9/.21/.79 | 70-100 100 | 10 90 |

TABLE I[1]-continued

Moly Catalysts from EG and Mixed Moly Sources Such as ADM and
Na$_2$MoO$_4$ or ADM and Na$_2$MoO$_4$.2H$_2$O - Incorporation of Sodium

| | | | | | | |
|---|---|---|---|---|---|---|
| 6032-17 | 11.33 | 0 | 64.53 | 11.5/.20/.80 | 73–100 | 18 |
| | (0.0693) | 0 | (0.2795) | | 100 | 80 |
| 5990-78 | 8.50 | 58.37 | 0 | 11.9/.16/.84 | 60–100 | 15 |
| | (0.0520) | (0.2844) | 0 | | 100 | 35 |
| 5990-79 | 8.50 | 0 | 68.57 | 11.5/.15/.85 | 40–100 | 20 |
| | (0.0520) | 0 | (0.2970) | | 100 | 35 |
| 5990-80 | 0 | 68.67 | 0 | 11.95/0/1 | 65–100 | 10 |
| | 0 | (0.3346) | 0 | | 100 | 30 |
| 5990-81 | 0 | 0 | 80.66 | 11.45/0/1 | 50–100 | 15 |
| | 0 | 0 | (0.3493) | | 100 | 45 |

| NB Run # | Quant BTMS % of the charge | % Moly (% Na) | % N$_2$ (% H$_2$O) | Acid # (% MOIN)[5] | Comments and Observations |
|---|---|---|---|---|---|
| 5990-65 Control | 92.07 | 11.70 (0.00) | 0.75 (1.80) | 134.28 (98.70) | Clear After 30 Min at 100° C. |
| 5990-66 | 90.22 | 12.10 (0.164) | 0.37 (2.04) | 131.91 (100.5) | Clear After 18 Min at 100° C. |
| 5990-67 | 87.79 | 11.90 (0.16) | 0.99 (0.92) | 134.13 (96.18) | Clear After 35 Min at 100° C. |
| 5990-68 | 92.26 | 11.50 (0.57) | 0.54 (0.68) | 121.96 (98.10) | Clear After 60 Min at 100° C. |
| 5990-69 | 87.67 | 12.10 (0.59) | 0.60 (1.94) | 127.09 (97.90) | Clear After 20 Min at 100° C. |
| 5990-70 | 91.97 | 11.80 (1.13) | 0.34 (0.95) | 109.20 (101.1) | After 100° C. Orange Few Solid |
| 5990-71 | 87.94 | 12.20 (1.19) | 0.35 (1.87) | 113.70 (99.82) | After Stripping Soln was Clear |
| 5990-72 | 87.75 | 12.20 (1.72) | 0.18 (0.99) | 98.02 (100.3) | After Stripping Still Few Solids |
| 6032-6 | 85.69 | 12.70 (1.70) | 0.21 (0.65) | 96.95 (102.1) | Cloudy After Strip-Filtered |
| 5990-73 | 89.72 | 11.90 (1.67) | 0.07 (1.62) | 96.80 (99.88) | After Stripping Soln was Clear |
| 6032-7 | 90.76 | 11.90 (1.57) | 0.08 (1.61) | 91.67 (101.2) | Clear After Strip no Solid |
| 5990-74 | 87.50 | 10.40 (1.89) | 0.10 (1.49) | 75.17 (85.88) | After Stripping Still Lot Solids |
| 6032-8 | 85.66 | 12.30 (2.15) | 0.18 (1.74) | 81.41 (99.46) | After Strip Still Lot Solids |
| 5990-75 | 83.96 | 10.30 (1.98) | 0.10 (1.97) | 73.78 (81.47) | After Stripping Still Some Solid |
| 6032-9 | 81.61 | 13.00 (2.23) | 0.19 (2.21) | 83.84 (99.95) | After Strip Still Some Solid |
| 6032-10 | 84.19 | 12.60 (2.83) | 0.16 (2.36) | 68.44 (101.0) | After Strip Still Few Solids |
| 6032-11 | 83.10 | 12.20 (2.61) | 0.03 (1.99) | 67.86 (96.27) | After Strip Still Lot Solids |
| 6032-12 | 83.55 | 11.40 (3.02) | 0.05 (2.94) | 56.36 (91.20) | After Strip Still Some Solids |
| 6032-13 | 77.91 | 11.50 (3.08) | 0.15 (3.48) | 50.68 (85.53) | After Strip Still Solids |
| 5990-76 | 82.59 | 8.86 (2.63) | 0.06 (2.41) | 41.19 (70.58) | After Stripping Still Some Solids |
| 6032-14 | 79.10 | 10.70 (2.97) | 0.14 (1.39) | 43.58 (81.74) | After Stripping Still Lot Solids |
| 5990-77 | 76.52 | 7.57 (2.52) | 0.11 (1.65) | 30.18 (55.66) | After Stripping Still Lot Solids |
| 6032-15 | 77.79 | 10.10 (2.70) | 0.05 (1.58) | 41.38 (75.52) | After Stripping Some Solids |
| 6032-16 | 74.92 | 8.60 (3.04) | 0.04 (2.11) | 29.71 (62.69) | After Stripping Lots of Solids |
| 6032-17 | 76.74 | 8.10 (2.55) | 0.03 (1.91) | 27.14 (60.22) | After Stripping Lots of Solids |
| 5990-78 | 78.92 | 7.60 (1.52) | 0.07 (2.04) | 22.06 (58.52) | Lots of Solids |
| 5990-79 | 75.18 | 7.34 (2.65) | 0.08 (2.44) | 23.16 (53.58) | Lots of Solids |
| 5990-80 | 72.40 | 5.00 (2.62) | 0.05 (1.54) | 3.27 (35.69) | After Stripping Still Lot Solids |
| 5990-81 | 78.80 | 4.50 (2.42) | 0.10 (3.26) | 0.96 (34.76) | After Stripping Still Lot Solids |

[1]In all of the examples, 248 grams (0.4 mol) of ethylene glycol was used. In each instance, the reaction was run at 100° C. for 1 hour.
[2]ADM analyzed 58.65% moly - ave. of 2 analyses.
[3]Na$_2$MoO$_4$ analyzed 46.75% moly - .2H$_2$O 41.55%
[4]GAMoly = Gram atoms molybdenum.
[5]% MOIN = % of charged molybdenum incorporated into the catalyst solution.

With reference to Table I it is to be noted that in the first 16 examples after the control run (5990-66 through 6032-11), the gram atoms of molybdenum derived from the ammonium dimolybdate was equal to the gram atoms of molybdenum derived from the sodium molybdate (6032-11) or more (i.e., a ratio of 19/1 in example 5990-66 down to a ratio of 1/1 in examples 6032-10 and 6032-11 (sometimes referred to hereafter as the Molybdenum Ratio.) The molybdenum/sodium/ethylene glycol complexes of the first 16 examples after the control run were found to effectively catalyze the reaction of tert. butyl hydroperoxide with propylene to provide tert. butyl alcohol and propylene oxide. Note that the acid number of these complexes progressively decreased as the Molybdenum Ratio decreased from 19/1 to 1/1 from an acid number of 131.91 (run 5990-66) to an acid number of 67.86 (run 6032-11). Note also that the percentage of molybdenum incorporated into the molybdenum/sodium/ethylene glycol complex was 90% or more, and usually close to 100% of the molybdenum that was charged to the reactor. Anomalous results (low percent molybdenum incorporated) were obtained in runs 5990-74 and 5990-75 which are believed to be analytical errors. It is to be further noted that most of the solutions were clear, but that in some instances solids were present. These solids, which were removed by filtration, were of unknown composition, but contained little, if any, molybdenum as shown by the analysis for percent molybdenum incorporated, as pointed out above.

In contrast, the complexes of examples 6032-12 through 5990-81 (Table I) were not active as catalysts. They all had acid numbers of less than about 60 and contained solids after stripping. Also, the percent of molybdenum incorporated into the catalyst rapidly dropped below the 90% level, thus demonstrating that molybdenum was in the solids and was lost from the system after filtration.

Example 4 (Run 5990-82, Table II)

To a 500-ml flask fitted with a mechanical stirrer, thermometer, $N_2$ pad, K-head and condenser and three necked receiver flask was added 248.0 g EG (4.0 moles), 51.0 g ADM (Analyzed for 59.1% molybdenum, 0.3142 g atoms of molybdenum), and 10.94 g $K_2MoO_4.5H_2O$ (analyzed for 40.6% molybdenum and 31.1% K, 0.0463 g atoms molybdenum in the 10.94 g $K_2MoO_4.5H_2O$).

The reaction mixture was heated to 100° C. from ambient temperature in 15 minutes. The reaction mixture was held at 100° C. for 1 hour (contained a few solids at this point) and then cooled to 65° C. (requiring 18 minutes). A vacuum was pulled (35 mm) and heating began at 10:53 AM. In fifteen minutes the temperature had been raised to 100° C. (30 mm pressure) and water was removed for another 12 minutes at 100° C. (25 mm, ultimate vacuum). The product was cooled—contained no solids. The overhead in flask receiver=19.5 g (29.78% $H_2O$).

The cold trap contained=2.0 g (87.80% $H_2O$).

The product weighed=283.5 g (% $H_2O$=1.83%; Acid number=116.19; % $N_2$=0.48%; % Moly=12.6%; K=1.28).

Example 5 (Run 5990-85, Table II)

In an experiment exactly like Example 4, 248.0 g ethylene glycol was reacted with 34.0 g ADM and 43.75 g $K_2MoO_4.5H_2O$. The procedure and product workup was essentially identical. The product contained 13.50% molybdenum and 4.99% K as well as 0.88% $N_2$, and 2.23% $H_2O$ and held an acid number of 80.13 mg KOH/g sample. The catalyst required no filtration and the product weighed 282.1 g, the cold trap weighed 1.8 g (84.75% $H_2O$) and the overhead contained 36.5 g (21.0% $H_2O$). The product weighed 282.1 g.

Example 6 (Run 6032-21, Table II)

In an experiment like Example 4, except 237.7 g EG was reacted with 17.0 g ADM and 55.6 g $K_2MoO_4$. The procedure and product work up was identical to that of Example 4. The product weighed 254.5 g and was analyzed by AA and found to contain 12.0% molybdenum and 6.90% K, 0.03% $N_2$ (Kjeldahl) and 1.94% $H_2O$ (Karl Fischer), and the acid number was reduced to 44.96 mg KOH/g sample.

Example 7 (Control Run (Run) 5990-65, Table II) (No Moly Compound Used Other Than ADM)

The product weighed 280.5 g and contained 11.70% molybdenum (AA). The % $N_2$ was 0.75%; % $H_2O$=1.80% and the acid number was 134.28.

TABLE II[1]

Molybdenum Complexes From EG and Mixed Molybdenum Sources Such as ADM and $K_2MoO_4.5H_2O$ - Incorporation of Potassium

| NB Run # | EG Grams (Moles) | ADM Grams (GAMoly)[6] | $K_2MoO_4.5H_2O$ Grams (GAMoly)[6] | Moles EG/ GAMoly ADM/ GAMoly From $K_2MoO_4$[6] | Stripping Condition Temp | Time | Quant. BTMS-F % of the Charge | % Moly (% K) | % $N_2$ (% $H_2O$) | Acid # (% MOIN)[7] |
|---|---|---|---|---|---|---|---|---|---|---|
| 5990-65 Control No K | 248.0 (4.0) | 56.67 (0.3466) | 0 0 | 11.54/1/0 | 50-100 100 | 15[2] 10 | 92.07 | 11.70 (0.00) | 0.75 (1.80) | 134.28 (98.70) |
| 5990-82 | 248.0 (4.0) | 51.00 (0.3142) | 10.94 A (0.0463) | 11.10/.87/.13 | 65-100 100 | 15[3] 12 | 91.48 | 12.60 (1.28) | 0.48 (1.83) | 116.19 (103.4) |
| 5990-83 | 248.0 (4.0) | 45.33 (0.2790) | 21.88 A (0.0927) | 10.76/.75/.25 | 50-100 100 | 20[3] 25 | 91.43 | 12.70 (1.20) | 0.20 (2.00) | 106.72 (102.6) |
| 5990-84 | 248.0 (4.0) | 39.67 (0.2443) | 32.81 A (0.1388) | 10.44/.64/.36 | 63-100 100 | 12[4] 48 | 89.24 | 12.70 (3.00) | 0.03 (1.43) | 89.20 (98.80) |
| 6032-18 | 237.7 (3.83) | 34.00 (0.2094) | 31.75 B (0.1333) | 11.67/.61/.39 | 75-100 100 | 7[3] 75 | 87.96 | 11.60 (3.85) | 0.05 (1.62) | 83.23 (94.15) |
| 5990-85 | 248.0 (4.00) | 34.00 (0.2094) | 43.75 A (0.1851) | 10.14/.53/.47 | 35-100 100 | 10[3] 65 | 86.60 | 13.50 (4.99) | 0.88 (2.23) | 80.13 (100.6) |
| 6032-19 | 237.7 (3.83) | 28.30 (0.1743) | 39.70 B (0.1667) | 11.24/.51/.49 | 70-100 100 | 5[3] 80 | 89.92 | 11.60 (4.70) | 0.31 (1.35) | 65.94 (97.48) |
| 5990-86 | 248.0 (4.00) | 28.33 (0.1743) | 54.69 A (0.2315) | 9.86/.43/.57 | 55-100 100 | 10[3] 55 | 87.46 | 14.30 (6.06) | 0.95 (3.24) | 67.37 (106.3) |
| 6032-20 | 237.7 (3.83) | 22.70 (0.1398) | 47.60 B (0.1999) | 11.28/.41/.59 | 80-100 100 | 10[3] 65 | 88.41 | 11.10 (5.50) | 0.04 (1.93) | 56.36 (92.97) |
| 5990-87 | 248.0 | 22.67 | 65.63 A | 9.58/.34/.66 | 60-100 | 15[3] | 88.31 | 13.60 | 0.18 | 53.11 |

TABLE II[1]-continued

Molybdenum Complexes From EG and Mixed Molybdenum Sources Such as ADM and K₂MoO₄.5H₂O - Incorporation of Potassium

| NB Run # | EG Grams (Moles) | ADM Grams (GAMoly)[6] | K₂MoO₄.5H₂O Grams (GAMoly)[6] | Moles EG/ GAMoly ADM/ GAMoly From K₂MoO₄[6] | Stripping Condition Temp | Stripping Condition Time | Quant. BTMS-F % of the Charge | % Moly (% K) | % N₂ (% H₂O) | Acid # (% MOIN)[7] |
|---|---|---|---|---|---|---|---|---|---|---|
|  | (4.00) | (0.1399) | (0.2776) |  | 100 | 47 |  | (7.18) | (3.39) | (100.8) |
| 6032-21 | 237.7 | 17.00 | 55.60 B | 11.34/.31/.69 | 70–100 | 7[3] | 82.02 | 12.00 | 0.03 | 44.96 |
|  | (3.83) | (0.1047) | (0.2335) |  | 100 | 60 |  | (6.90) | (1.94) | (94.12) |
| 5990-88 | 248.0 | 17.00 | 76.56 A | 9.32/.24/.76 | 85–100 | 7[4] | 79.80 | 14.70 | 0.21 | 50.25 |
|  | (4.00) | (0.1048) | (0.3242) |  | 100 | 53 |  | (8.34) | (3.09) | (97.40) |
| 6032-22 | 237.7 | 11.30 | 63.50 B | 11.40/.21/.79 | 75–100 | 5[3] | 88.61 | 13.30 | 0.02 | 27.71 |
|  | (3.83) | (0.0696) | (0.2666) |  | 100 | 75 |  | (7.60) | (2.96) | (114.2) |
| 5990-89 | 248.0 | 8.50 | 92.96 A | 8.98/.12/.88 | 60–100 | 15[5] | 77.28 | 13.80 | 0.08 | 23.96 |
|  | (4.00) | (0.0523) | (0.3932) |  | 100 | 75 |  | (7.91) | (3.11) | (87.20) |
| 6032-23 | 237.7 | 5.70 | 71.40 B | 11.45/.10/.90 | 65–100 | 7[5] | 81.64 | 8.50 | 0.14 | 17.40 |
|  | (3.83) | (0.0351) | (0.2998) |  | 100 | 90 |  | (5.50) | (3.47) | (67.98) |

ADM used in the above catalyst preparations was analyzed by AA and found to contain 59.1% molybdenum.
A = K₂MoO₄.5H₂O was analyzed by AA and found to contain 40.6% molybdenum and 13.1% potassium.
B = K₂MoO₄ assay 99%, % molybdenum = 40.287 and % potassium = 32.838 by stoichiometry.
[1]All reactions ran at 100° C. for 1 hour.
[2]Clear after 30 minutes.
[3]Clear after stripping.
[4]A few solids after stripping.
[5]Solids after stripping.
[6]GAMoly = gram atoms molybdenum.
[7]% MOIN = % of charged molybdenum incorporated into the catalyst solution.

All experiments relating to the preparation of molybdenum/potassium/ethylene glycol complexes are summarized in Table II. As potassium is incorporated into the complexes, the acid number drops off sharply. Note from run 6032-19 (Table II) that when the ratio of gram atoms of molybdenum derived from ammonium dimolybdate to the gram atoms of molybdenum derived from potassium molybdate was about 1/1, the acid number was only 65.94 and dropped below an acid number of 60 thereafter, except for run 5990-86 (Table II), which is believed to be an anomalous analytical error.

The complexes of runs 5990-82 to 6032-19 (Table II) were active as catalysts in promoting the reaction of tert. butyl hydroperoxide with propylene to provide tert. butyl alcohol and propylene oxide, whereas the complexes of runs 5990-86 through 6032-23 were marginal, or ineffective, again indicating that when The Molybdenum Ratio is less than about 1/1, the complexes are not effective catalysts.

Example 8 (Run 6032-1, Table III)

In an example like Example 4, 74.4 g EG was reacted with 13.6 g ADM and 8.515 g Cs₂MoO₄. Workup and procedure was like that in Example 4. The product was clear and required no filtration and weighed 84.4 g. Analysis showed the product to contain 12.5% molybdenum and 2.34% Cs (AA) as well as 0.656% N₂ (Kjeldahl) and 1.50% H₂O (Karl Fischer) and had an acid number of 121.50 mg KOH/g sample.

Examples 9 and 10

In Example 9 (run 6032-4, Table III) we tried incorporation of lanthanum using La₂(MoO₄)₃ and ADM as molybdenum sources. After the digestion and vacuum stripping, there was a large volume of solids and the product filtered very slowly. The acid number was not reduced compared to the control run and the molybdenum value was substantially less than theoretical (17.57%). La2(MoO4)3 did not make a good molybdenum/lanthanum/ethylene glycol complex. In Example 10, run 6032-5 (Table III) we tried incorporation of barium using BaMoO₄ and ADM as the molybdenum sources. Although the acid number was slightly reduced (119.3) we found almost no barium in the product (<0.005%) and the product contained many solids after reaction at 100° C. and vacuum stripping. We judge BaMoO₄ did not incorporate well to form a molybdenum/barium/ethylene glycol complex.

The results are summarized in Table III.

TABLE III[1]

Molybdenum Catalysts from EG and Mixed Molybdenum Sources Such as ADM and CS₂MoO₄, La₂(MoO₄)₃ and BaMoO₄

| NB Run # | ADM Grams (GAMoly)[5] | CS₂MoO₄ Grams (GAMoly)[5] | Moles EG/ GAMoly ADM/ GAMoly From CS₂MoO₄[5] | Stripping Condition Temp | Stripping Condition Time | Quant BTMS-F % of the Charge | % Moly (% CS) | % N₂ (% H₂O) | Acid # (% MOIN)[6] |
|---|---|---|---|---|---|---|---|---|---|
| 6032-1 | 13.6 | 8.515 | 11.59/.81/.19 | 50–100 | 15[2] | 87.5 | 12.50 | 0.656 | 121.50 |
|  | (0.0838) | (0.0197) |  | 100 | 8 |  | (2.34) | (1.50) | (106.30) |
| 6032-2 | 11.9 | 12.773 | 11.66/.71/.29 | 40–100 | 20[3] | 86.0 | 11.60 | 0.480 | 121.03 |
|  | (0.0733) | (0.0296) |  | 100 | 10 |  | (3.30) | (0.15) | (100.17) |
| 6032-3 | 10.2 | 17.030 | 11.74/.61/.39 | 55–100 | 11[3] | 81.1 | 11.60 | 0.765 | 108.95 |
|  | (0.0628) | (0.0394) |  | 100 | 22 |  | (4.05) | (1.15) | (97.48) |

| NB Run # | ADM Grams (GAMoly)[5] | La₂(MoO₄)₃ Grams (GAMoly)[5] | Moles EG/ GAMoly ADM/ GAMoly From La₂(MoO₄)₃[5] | Stripping Condition Temp | Stripping Condition Time | Quant BTMS-F % of the Charge | % Moly (% LA) | % N₂ (% H₂O) | Acid # (% MOIN)[6] |
|---|---|---|---|---|---|---|---|---|---|
| 6032-4 | 11.9 | 7.576 | 11.62/.71/.29 | 80–100 | 10[4] | 60.1 | 13.80 | 1.090 | 136.24 |
|  | (0.0733) | (0.0300) |  | 100 | 42 |  |  | (1.74) | (78.55) |

TABLE III[1]-continued

Molybdenum Catalysts from EG and Mixed Molybdenum Sources
Such as ADM and $CS_2MoO_4$, $La_2(MoO_4)_3$ and $BaMoO_4$

| NB Run # | ADM Grams (GAMoly)[5] | $BaMoO_4$ Grams (GAMoly)[5] | Moles EG/ GAMoly ADM/ GAMoly From $BaMoO_4$[5] | Stripping Condition Temp | Time | Quant BTMS-F % of the Charge | % Moly (% BA) | % $N_2$ (% $H_2O$) | Acid # (% MOIN)[6] |
|---|---|---|---|---|---|---|---|---|---|
| 6032-5 | 13.6 (0.0838) | 5.946 (0.0200) | 11.59/.81/.19 | 30–100 100 | 15[4] 55 | 74.9 | 11.00 <0.005 | 2.000 (0.62) | 119.29 (77.77) |

ADM used in these catalyst preparations was analyzed by AA and found to contain 59.1% molybdenum.
Cesium molybdate was analyzed by AA and found to contain 22.2% molybdenum and 24.2% cesium.
Lanthanum molybdate was not analyzed by AA - % molybdenum based on formula = 37.99% molybdenum.
Barium molybdate was not analyzed by AA - % molybdenum based on formula = 32.27% molybdenum.
[1]74.4 Grams (1.2 moles) of ethylene glycol was used for each of the runs. Each of the reactions was conducted at 100° C. for 1 hour.
[2]Clear after stripping.
[3]Clear after stripping, solids precipitated.
[4]Solids found after stripping.
[5]GAMoly = gram atoms molybdenum.
[6]% MOIN = % of charged molybdenum incorporated into the catalyst solution.

Use of Molybdenum/Alkali Metal/Ethylene Glycol Complexes as Catalysts

Experimental Procedure (e.g., Run 6000-60, Table IV)

To a nitrogen purged 300 ml 316 stainless steel autoclave was added 45.0 g propylene followed by a solution of TBHP/TBA/moly catalyst made by mixing 130.86 g of TBHP/TBA (that was 72.36% TBHP, 27.44% TBA, and 0.20% $H_2O$) with 0.44 grams of sodium/molybdenum/EG catalyst (5990-72) containing 12.20% molybdenum and 1.72% Na. The reaction mixture was heated to 120° C. over a 30 minute period and held at 120° C. for 2.0 hours. The reaction mixture was cooled and a sample removed under 300 psig pressure for GLC analysis. The rest of the effluent was pressured out into a bomb at 500 psig. The latter sample (117.6 g) was stripped of propylene and weighed 102.8 g. The ratio of liquid to total product in the stripped sample can be applied to calculate the total weight of liquid product $102.8/117.6 = X/1.763$
X = weight liquid product (total) = 154.11
Weight of total product = 176.3 g The liquid product was analyzed for percent TBHP remaining = 8.27%. The liquid product contained 309 ppm molybdenum. The glc analysis showed 5.014% propylene, 0.226% $H_2O$, 0.023% unknowns, 0.046% methanol, 28.455% propylene oxide, 0.182% acetone, 0.092% isopropanol, 65.731% TBA/TBHP, 0.012% PG, 0.024% unknown and 0.096% propylene glycol t-butyl ether. The selectivity to PO basis TBHP reacted was 95.0% and the TBHP conversion was 86.5%. The moly recovery was 91.4% and the sum of all unknowns after TBA/TBHP = 0.13%. There was only 1 ppm propylene dimer, basis pure PO.

The results of the runs that were made are summarized in the following tables.

TABLE IV[1]

Propylene Oxide Batch Runs, Epoxidation Reactor

| Run No. | Temp (C) | Time (Hr) | Catalyst Conc. Wt. % | Catalyst Notebook No. | Molar Ratio $C_3$:HP | PO Conc. | Yield | Selec. TBHP to PO | TBHP Conv. | $C_3$ Dim ppm | Unks. (Heavies) |
|---|---|---|---|---|---|---|---|---|---|---|---|
| *Runs 5980-74A, -78A, -76A, -80A, -85A, -91A, -86A and 92A used EG + AHM cat Acid # = 167.85, $H_2O$ = 1.67% (8.64/1) ||||||||||||
| Runs 6000-64A, -65A, -66A and -67A used EG + ADM + $Na_2MoO_4$·$2H_2O$ cat with Acid # = 113.70, $H_2O$ = 1.87% (12/.8/.2) ||||||||||||
| Runs 6000-60A, -61A, -62A and -63A used EG + ADM + $Na_2MoO_4$ cat with Acid # = 98.02, $H_2O$ = 0.99% (12/.7/.3) ||||||||||||
| Runs 6000-68A, -69A, -70A and -71A used EG + ADM + $Na_2MoO_4$ cat with Acid # = 75.17, $H_2O$ = 1.49% (12/.6/.4) ||||||||||||
| 5980-74A* | 120 | 2.0 | .0355 | 5855-50-3 | 1.01 | 30.65 | 88.38 | 92.54 | 95.50 | 3 | 1.12 |
| 5980-78A* | 120 | 2.0 | .0349 | 5855-50-3 | .98 | 29.19 | 83.65 | 90.58 | 92.35 | 1 | 1.13 |
| 6000-64A | 120 | 2.0 | .0304 | 5990-71 | 1.00 | 30.04 | 86.52 | 97.34 | 88.89 | 1 | .28 |
| 6000-60A | 120 | 2.0 | .0295 | 5990-72 | 1.01 | 28.46 | 82.21 | 94.99 | 86.54 | 1 | .13 |
| 6000-68A | 120 | 2.0 | .0304 | 5990-74 | 1.01 | 27.88 | 80.46 | 96.61 | 83.28 | 5 | .03 |
| 5980-76A* | 120 | 2.0 | .0353 | 5855-50-3 | 1.34 | 30.30 | 94.64 | 96.28 | 98.29 | 11 | .90 |
| 5980-80A* | 120 | 2.0 | .0347 | 5855-50-3 | 1.31 | 30.41 | 94.36 | 96.02 | 98.27 | 11 | .68 |
| 6000-65A | 120 | 2.0 | .0308 | 5990-71 | 1.29 | 30.04 | 92.74 | 97.65 | 94.97 | 6 | .30 |
| 6000-61A | 120 | 2.0 | .0301 | 5990-72 | 1.29 | 29.20 | 90.18 | 98.07 | 91.95 | 6 | .26 |
| 6000-69A | 120 | 2.0 | .0302 | 5990-74 | 1.29 | 27.61 | 85.44 | 96.06 | 88.95 | 8 | .02 |
| 5980-85A | 110 130 | 1.0 1.0 | .0355 | 5855-50-3 | 1.29 | 30.22 | 93.37 | 94.88 | 98.41 | 45 | .86 |
| 5980-91A | 110 130 | 1.0 1.0 | .0355 | 5855-50-3 | 1.26 | 30.41 | 93.18 | 94.64 | 98.46 | 18 | .93 |
| 6000-66A | 110 130 | 1.0 1.0 | .0302 | 5990-71 | 1.31 | 30.11 | 93.36 | 97.67 | 95.59 | 11 | .30 |
| 6000-62A | 110 130 | 1.0 1.0 | .0295 | 5990-72 | 1.30 | 29.42 | 91.15 | 96.99 | 93.97 | 7 | .32 |
| 6000-70A | 110 130 | 1.0 1.0 | .0304 | 5990-74 | 1.30 | 29.11 | 90.12 | 98.33 | 91.65 | 8 | .04 |
| 5980-86A | 110 | 1.0 | .0351 | 5855-50-3 | 1.60 | 28.51 | 94.52 | 95.36 | 99.12 | 183 | .70 |

TABLE IV-continued

| | | | Propylene Oxide Batch Runs, Epoxidation Reactor | | | | | | | | |
|---|---|---|---|---|---|---|---|---|---|---|---|
| | | | Catalyst | | Molar | | | Selec. | | C₃ | |
| Run No. | Temp (C) | Time (Hr) | Conc. Wt. % | Notebook No. | Ratio C₃:HP | PO Conc. | Yield | TBHP to PO | TBHP Conv. | Dim ppm | Unks. (Heavies) |
| 5980-92A | 130 110 130 | 1.0 1.0 1.0 | .0349 | 5855-50-3 | 1.59 | 28.86 | 95.37 | 96.13 | 99.21 | 179 | .60 |
| 6000-67A | 110 130 | 1.0 1.0 | .0302 | 5990-71 | 1.59 | 28.83 | 95.27 | 97.41 | 97.81 | 34 | .23 |
| 6000-63A | 110 130 | 1.0 1.0 | .0301 | 5990-72 | 1.58 | 28.47 | 93.95 | 98.32 | 95.56 | 20 | .28 |
| 6000-71A | 110 130 | 1.0 1.0 | .0302 | 5990-74 | 1.59 | 27.73 | 91.77 | 98.13 | 93.52 | 17 | .18 |

*Control Runs - No sodium in catalyst
[1]The molar ratio of tert.butyl hydroperoxide to tert.butyl alcohol was 2.17
[2]Staged runs; 1 hour of reaction at 110° C. (first stage) followed by 1 hour of reaction at 130° C.

In Table IV, the first series of runs 5980-74A and 5980-78A are control runs using molybdenum/ethylene glycol complexes that did not contain sodium. Note that the selectivity of tert. butyl hydroperoxide to propylene oxide was about 90 to 92% (analytical results have a margin of error of about ±0.5%). The unknown heavy by-products were in excess of 1%. In contrast, in runs 6000-64A, 6000-60A and 6000-68A, wherein a catalyst of the present invention was used, an improved selectivity of about 95-97% was observed and a decrease in heavies to about 0.3% or less.

In the next series of runs, runs 5980-76A through 6000-69A, wherein the charge ratio of propylene to tert. butyl hydroperoxide was increased from about 1/1 to about 1.3/1, there was less of an increase in the selectivity to propylene oxide when control runs 5980-76A and 5980-80A are compared with runs 6000-65A, 6000-61A and 6000-60A, using molybdenum/sodium ethylene glycol complexes of the present invention. Again, however, there is a significant decrease in the yield of undesirable unknown heavy by-products.

The same pattern is evident in staged runs 5980-85A through 6000-70A and the staged runs 5980-86A through 6000-71A.

TABLE V[1]

Propylene Epoxidation - Comparison of Results from Using Na—Moly-EG Catalysts vs. K—Moly-EG Catalysts vs. Moly-EG-Catalysts

| Notebook No. | Catalyst Description | | Acid # | Mole Ratio = C₃/TBHP | Wt. % PO in Total Eff. | PO Sel. % Basis TBHP Reacted | TBHP Conv % | Sum of Unknown After PG (Hvys) Wt. % | ppm C₃⁼ Dimer Pure PO Basis |
|---|---|---|---|---|---|---|---|---|---|
| | Reactants | | | | | | | | |
| 5980-74A | EG + ADM | | 168 | 1.01 | 30.6 | 92.5 | 95.5 | 1.12 | 3 |
| 5980-78A | " | | 168 | 0.98 | 29.2 | 90.6 | 92.4 | 1.13 | 1 |
| 6000-72A | EG + ADM + K₂MoO₄ | | 116 | 1.01 | 29.5 | 93.2 | 89.6 | 0.38 | 1 |
| 6000-64A | EG + ADM + Na₂MoO₄ | | 114 | 1.00 | 30.0 | 97.3 | 88.9 | 0.28 | 1 |
| 6000-60A | " | | 98 | 1.01 | 28.5 | 95.0 | 86.5 | 0.13 | 1 |
| 6000-76A | EG + ADM + K₂MoO₄ | | 80 | 1.01 | 13.2 | 87.5 | 42.7 | 0.02 | 65 |
| 6000-68A | EG + ADM + Na₂MoO₄ | | 75 | 1.01 | 27.9 | 96.6 | 83.3 | 0.03 | 5 |
| 6000-82A | " | | 75 | 1.03 | 26.4 | 95.9 | 78.4 | 0.12 | 3 |
| 6000-84A | " | | 68 | 1.02 | 22.5 | 95.4 | 67.1 | 0.05 | 8 |
| 6000-80A | EG + ADM + K₂MoO₄ | | 50 | 1.03 | 5.6 | 70.5 | 22.75 | 0.02 | 156 |
| 5980-76A | EG + ADM | | 168 | 1.34 | 30.3 | 96.3 | 98.3 | 0.90 | 11 |
| 5980-80A | " | | 168 | 1.31 | 30.4 | 96.0 | 98.3 | 0.68 | 11 |
| 6000-73A | EG + ADM + K₂MoO₄ | | 116 | 1.25 | 30.1 | 96.8 | 93.4 | 0.42 | 4 |
| 6000-65A | EG + ADM + Na₂MoO₄ | | 114 | 1.29 | 30.0 | 97.6 | 95.0 | 0.30 | 6 |
| 6000-61A | " | | 98 | 1.29 | 29.2 | 98.1 | 92.0 | 0.26 | 6 |
| 6000-77A | EG + ADM + K₂MoO₄ | | 80 | 1.29 | 13.8 | 88.5 | 47.3 | 0.11 | 36 |
| 6000-69A | EG + ADM + Na₂MoO₄ | | 75 | 1.29 | 27.6 | 96.1 | 89.0 | 0.02 | 8 |
| 6000-83A | " | | 75 | 1.30 | 27.0 | 99.2 | 82.7 | 0.11 | 9 |
| 6000-85A | " | | 68 | 1.30 | 22.4 | 96.9 | 70.5 | 0.04 | 18 |

[1]All reactions were run at 120° for 2 hrs.

TABLE VI

Propylene Epoxidation - Comparison of Results from Using Na—Moly-EG Catalysts vs. K—Moly-EG Catalysts vs. Moly-EG-Catalysts

| Notebook No. | Epoxidation Reaction Condition | Catalyst Description Reactants | Acid # | Mole Ratio = C₃/TBHP | Wt. % PO in Total Eff. | PO Sel. % Basis TBHP Reacted | TBHP Conv % | Sum of Unknown After PG (Hvys) Wt. % | ppm C₃⁼ Dimer Pure PO Basis |
|---|---|---|---|---|---|---|---|---|---|
| 5980-85A | 110°, 1 hr 130°, 1 hr | EG + AHM | 168 | 1.29 | 30.2 | 94.9 | 98.4 | 0.86 | 45 |
| 5980-91A | 110°, 1 hr 130°, 1 hr | " | 168 | 1.26 | 30.4 | 94.6 | 98.5 | 0.93 | 18 |
| 6000-74A | 110°, 1 hr 130°, 1 hr | EG + ADM + K₂MoO₄ | 116 | 1.25 | 30.7 | 97.6 | 94.6 | 0.40 | 7 |

TABLE VI-continued

Propylene Epoxidation - Comparison of Results from Using Na—Moly-EG Catalysts vs. K—Moly-EG Catalysts vs. Moly-EG-Catalysts

| Notebook No. | Epoxidation Reaction Condition | Catalyst Description Reactants | Acid # | Mole Ratio = $C_3$/TBHP | Wt. % PO in Total Eff. | PO Sel. % Basis TBHP Reacted | TBHP Conv % | Sum of Unknown After PG (Hvys) Wt. % | ppm $C_3^=$ Dimer Pure PO Basis |
|---|---|---|---|---|---|---|---|---|---|
| 6000-66A | 110°, 1 hr / 130°, 1 hr | EG + ADM + $Na_2MoO_4$ | 114 | 1.31 | 30.1 | 97.7 | 95.6 | 0.30 | 11 |
| 6000-62A | 110°, 1 hr / 130°, 1 hr | " | 98 | 1.30 | 29.4 | 97.0 | 94.0 | 0.32 | 7 |
| 6000-78A | 110°, 1 hr / 130°, 1 hr | EG + ADM + $K_2MoO_4$ | 80 | 1.30 | 13.7 | 83.4 | 49.8 | 0.15 | 71 |
| 6000-70A | 110°, 1 hr / 130°, 1 hr | EG + ADM + $Na_2MoO_4$ | 75 | 1.30 | 29.1 | 98.3 | 91.6 | 0.04 | 8 |
| 5980-86A | 110°, 1 hr / 130°, 1 hr | EG + AHM | 168 | 1.60 | 28.5 | 95.4 | 99.1 | 0.70 | 183 |
| 5980-92A | 110°, 1 hr / 130°, 1 hr | " | 168 | 1.59 | 28.9 | 96.1 | 99.2 | 0.60 | 179 |
| 6000-75A | 110°, 1 hr / 130°, 1 hr | EG + ADM + $K_2MoO_4$ | 116 | 1.60 | 29.4 | 98.0 | 97.7 | 0.33 | 18 |
| 6000-67A | 110°, 1 hr / 130°, 1 hr | EG + ADM + $Na_2MoO_4$ | 114 | 1.59 | 28.8 | 97.4 | 97.8 | 0.23 | 34 |
| 6000-63A | 110°, 1 hr / 130°, 1 hr | " | 98 | 1.58 | 28.5 | 98.3 | 95.6 | 0.28 | 20 |
| 6000-79A | 110°, 1 hr / 130°, 1 hr | EG + ADM + $K_2MoO_4$ | 80 | 1.59 | 12.6 | 87.8 | 46.9 | 0.15 | 144 |
| 6000-71A | 110°, 1 hr / 130°, 1 hr | EG + ADM + $Na_2MoO_4$ | 75 | 1.59 | 27.7 | 98.1 | 93.5 | 0.18 | 17 |

In Table IV, runs 5980-74A and 5980-78A are control runs using a molybdenum/ethylene glycol complex containing no sodium or potassium. Runs 6000-72A and 6000-64A are comparison runs, at about the same acid number comparing a molybdenum/sodium/ethylene glycol complex with a molybdenum/potassium/ethylene glycol complex. Note that there was an increase in propylene oxide selectivity in both runs compared to epoxidation with molybdenum-EG catalyst containing no potassium or sodium, but that the sodium-containing complex was clearly superior to the potassium-containing complex. This is even more evident in runs 6000-60A and 6000-76A. Runs 6000-68A, 6000-82A and 6000-84A, using sodium-containing complexes having acid numbers of 68 and 75 gave good results whereas poor results were obtained in run 6000-80A using a potassium-containing complex having an acid number of 50.

The same pattern is evident in runs 5980-76A through 6000-85A which differ from runs 5980-74A through 6000-80A in that a higher ratio of propylene to tert. butyl hydroperoxide was employed (1.3/1 vs. 1/1). Again, the sodium-containing complexes gave a better selectivity to propylene oxide while producing less propylene dimer and less unknown heavies than the potassium-containing complexes.

Staged runs 5980-85A through 6000-70A were conducted using a mole ratio of propylene to tert. butyl hydroperoxide of about 1.3 and staged runs 5980-86A through 6000-71A were conducted using a mole ratio of propylene to tert. butyl hydroperoxide of about 1.6 to 1. Once again, the results obtained using the sodium-containing complexes were better than the results obtained using the potassium-containing complexes, particularly at the lower acid numbers. In runs 6000-78A and 600-79A where the potassium-containing complex that was used had an acid number of about 80, the selectivity to propylene oxide was poor; propylene dimer production was about equivalent to that of control runs 5980-85A, 5980-91A, 5980-86A and 5980-92A but, significantly, the production of unknown heavies in runs 6000-78A and 6000-79A was much lower than in control runs 5980-85A, 5980-91A, 5980-86A and 5980-92A.

The results reported in Tables IV, V and VI demonstrate that the complexes of the present invention are superior catalysts as compared with the conventional control catalysts. The separation of unwanted propylene dimer by-products from propylene oxide is difficult and expensive, and the loss of propylene to unknown heavies adversely affects the overall economics of the process. Although the use of higher ratios of propylene to tert. butyl hydroperoxide improves selectivity to propylene oxide, this also increases the amounts of propylene dimer and unknown heavies that are formed. Thus, by-product formation frequently limits the ratio of propylene to tert. butyl hydroperoxide that can be used. However, the significant reductions in propylene dimer and unknown heavies yields that are obtained with the catalyst complexes of the present invention can be exploited in commercial operations by using higher propylene to tert. butyl hydroperoxide ratios for given levels of propylene dimer and unknown heavies formation.

The complexes and method of this invention, as particularly illustrated by the foregoing examples, should not be construed as limiting the scope of this invention.

We claim:

1. A clear, storage stable solution of a molybdenum-/alkali metal/ethylene glycol complex in ethylene glycol made by the process comprising:

reacting at an elevated temperature between about 25° and 150° C. a solid ammonium molybdate or a hydrate thereof and a solid alkali metal molybdate or a hydrate thereof with ethylene glycol, such that the ratio of moles of ethylene glycol to total gram atoms of molybdenum in said molybdates ranges from about 7:1 to 10:1, and the ratio of gram atoms of molybdenum in said ammonium molybdate or hydrate thereof to gram atoms of molybdenum in said alkali metal molybdate is from about 1:1 to about 20:1 to thereby provide a reaction product composed of a solution of an alkali metal-containing complex of molybdenum, alkali metal and ethylene glycol and by-products, including water, in said ethylene glycol and subsequently stripping said solution at a reduced pressure to remove from about 5 to about 25% of said reaction product, as distillate, to thereby provide a storage stable solution of said complex in said ethylene glycol having a molybdenum content of about 6 wt. % to about 20 wt. %, a water concentration of about 0.1 wt. % to about 6 wt. % and an acid number of more than about 60.

2. A storage stable solution as in claim 1 wherein the alkali metal molybdate is a sodium molybdate.

3. A storage stable solution as in claim 1 wherein the alkali metal molybdate is a potassium molybdate.

4. A method of preparing a catalytically active storage stable solution of a molybdenum/alkali metal/ethylene glycol complex in ethylene glycol which comprises reacting at an elevated temperature between about 25° and 150° C. a solid ammonium molybdate or a hydrate thereof and a solid alkali metal molybdate or a hydrate thereof with ethylene glycol, such that the ratio of moles of ethylene glycol to total gram atoms of molybdenum in said molybdates ranges from about 7:1 to 20:1, and the ratio of gram atoms of molybdenum in said ammonium molybdate or hydrate thereof to gram atoms of molybdenum in said alkali metal molybdate is from about 1:1 to about 20:1 to thereby provide a reaction product composed of a solution of a complex of molybdenum, alkali metal and ethylene glycol and by-products, including water in said ethylene glycol and subsequently stripping said solution at a reduced pressure to remove from about 5 to about 25% of said reaction product, as distillate, to thereby provide a storage stable solution of said complex in said ethylene glycol having a molybdenum content of about 6 wt. % to about 20 wt. %, a water concentration of about 0.1 wt. % to about 6wt. % and an acid number of more than about 60.

5. A method as in claim 4 wherein the alkali metal molybdate is a sodium molybdate.

6. A method as in claim 4 wherein the alkali metal molybdate is a potassium molybdate.

7. A clear, storage stable solution of a molybdenum/alkali metal/ethylene glycol complex in ethylene glycol made by the process comprising:

reacting a solid ammonium molybdate or a hydrate thereof and a solid alkali metal molybdate or a hydrate thereof with ethylene glycol, such that the ratio of moles of ethylene glycol to total gram atoms of molybdenum in said molybdates ranges from about 8:1 to 16:1, and the ratio of gram atoms of molybdenum in said ammonium molybdate or hydrate thereof to gram atoms of molybdenum in said alkali metal molybdate is from about 1:1 to about 20:1 under reaction conditions including an elevated temperature between about 90° and 120° C. and a reaction time of about 0.2 and about 2 hours to thereby provide a reaction product composed of a solution of an alkali metal-containing complex of molybdenum, alkali metal and ethylene glycol and by-products, including water, in said ethylene glycol and subsequently stripping said solution at a reduced pressure of about 10 to about 100 mm Hg for a time sufficient to remove from about 5 to about 25% of said reaction product, as distillate, to thereby provide a storage stable solution of said complex in said ethylene glycol having a molybdenum content of about 10 wt. % to about 20 wt. %, a water concentration of about 0.1 wt. % to about 6 wt. % and an acid number of more than about 60.

8. A solution as in claim 7 wherein the ammonium molybdate is ammonium dimolybdate or ammonium heptamolybdate and the akali metal molybdate is sodium molybdate, sodium molybdate dihydrate or potassium molybdate pentahydrate.

9. A solution as in claim 8 wherein the ammonium molybdate is ammonium dimolybdate and the alkali metal is sodium molybdate.

10. A solution as in claim 8 wherein the ammonium molybdate is ammonium dimolybdate and the alkali metal is sodium molybdate dihydrate.

11. A solution as in claim 8 wherein the ammonium molybdate is ammonium dimolybdate and the alkali metal is potassium molybdate pentahydrate.

12. A method of preparing a catalytically active storage stable solution of a molybdenum/alkali metal/ethylene glycol complex in ethylene glycol which comprises reacting a solid ammonium molybdate or a hydrate thereof and a solid alkali metal molybdate or a hydrate thereof with ethylene glycol, such that the ratio of moles of ethylene glycol to total gram atoms of molybdenum in said molybdates ranges from about 8:1 to 16:1, and the ratio of gram atoms of molybdenum in said ammonium molybdate or hydrate thereof to gram atoms of molybdenum in said alkali metal molybdate is from about 1:1 to about 20:1 under reaction conditions including an elevated temperature between about 90° and 120° C. and a reaction time of abut 0.2 to about 2 hours to thereby provide a reaction product composed of a solution of an alkali metal-containing complex of molybdenum, alkali metal and ethylene glycol and by-products, including water, in said ethylene glycol and subsequently stripping said solution at a reduced pressure of about 10 to 100 mm Hg for a time sufficient to remove from about 5 to about 25% of said reaction product, as distillate, to thereby provide a storage stable solution of said complex in said ethylene glycol having a molybdenum content of about 10 wt. % to about 20 wt. %, a water concentration of about 0.1 wt. % to about 6 wt. % and an acid number of more than about 60.

13. A method as in claim 12 wherein the ammonium molybdate is ammonium dimolybdate or ammonium heptamolybdate and the alkali metal molybdate is sodium molybdate, sodium molybdate dihydrate or potassium molybdate pentahydrate.

14. A method as in claim 13 wherein the ammonium molybdate is ammonium dimolybdate and the alkali metal is sodium molybdate.

15. A method as in claim 13 wherein the ammonium molybdate is ammonium dimolybdate and the alkali metal is sodium molybdate dihydrate.

16. A method as in claim 13 wherein the ammonium molybdate is ammonium dimolybdate and the alkali metal is potassium molybdate pentahydrate.

* * * * *